US008293779B2

United States Patent
Konofal

(10) Patent No.: US 8,293,779 B2
(45) Date of Patent: Oct. 23, 2012

(54) MAZINDOL COMBINATION IN THE TREATMENT OF ATTENTION DEFICIT/HYPERACTIVITY

(75) Inventor: Eric Konofal, Senlis (FR)

(73) Assignee: Assistance Publique-Hopitaux de Paris, Paris (FR)

( * ) Notice: Subject to any disclaimer, the term of this patent is extended or adjusted under 35 U.S.C. 154(b) by 499 days.

(21) Appl. No.: 12/296,900

(22) PCT Filed: Apr. 11, 2007

(86) PCT No.: PCT/EP2007/053512
§ 371 (c)(1),
(2), (4) Date: Oct. 10, 2008

(87) PCT Pub. No.: WO2007/116076
PCT Pub. Date: Oct. 18, 2007

(65) Prior Publication Data
US 2009/0136593 A1 May 28, 2009
US 2011/0223260 A2 Sep. 15, 2011

(30) Foreign Application Priority Data

Apr. 11, 2006 (FR) .................................... 06 03197

(51) Int. Cl.
*A61K 31/416* (2006.01)
*A61K 33/26* (2006.01)
*A01N 43/52* (2006.01)
*A01N 59/16* (2006.01)
(52) U.S. Cl. ....................................... 514/393; 424/646
(58) Field of Classification Search .................. None
See application file for complete search history.

(56) References Cited

U.S. PATENT DOCUMENTS

| | | | | |
|---|---|---|---|---|
| 4,148,906 A * | 4/1979 | Collipp | | 514/393 |
| 6,217,904 B1 * | 4/2001 | Midha et al. | | 424/468 |
| 2002/0161002 A1 * | 10/2002 | Epstein et al. | | 514/220 |
| 2006/0147552 A1 * | 7/2006 | Konofal | | 424/646 |

FOREIGN PATENT DOCUMENTS

| | | |
|---|---|---|
| GB | 2144410 A1 | 3/1985 |
| WO | 91/11184 | 8/1991 |
| WO | 93/21917 | 11/1993 |
| WO | 02/053104 | 7/2002 |
| WO | 2004/091546 | 10/2004 |

OTHER PUBLICATIONS

Attention Deficit Hyperactivity Disorder. National Institute of Mental Health 2008.*
Mortensen et al. (European Journal of Pharmacology 2003, 479, 159-170).*
Lin (The Pharmacogenomics Journal 2003, 3, 159-168).*
Walter (Drug Development Research 2005, 65, 97-118).*
Bruner et al. (Lancet 1996, 348, 992).*
Mazindol, Toxnet; National Library of Medicine 2006.*
Biederman, J., et al., Efficacy and safety of modafinil film-coated tablets in children and adolescents with attention-deficit/hyperactivity disorder: results of a randomized, double-blind, placebo-controlled, flexible-dose study, Pediatrics. Dec. 2005;116(6):e777-84.
Biederman, J., et al., Efficacy of atomoxetine versus placebo in school-age girls with attention-deficit/hyperactivity disorder, Pediatrics. Dec. 2002;110(6):e75.
Busby, K., et al., Sleep patterns in hyperkinetic and normal children, Sleep. 1981;4(4):366-83.
Carskadon, M. A., et al., The multiple sleep latency test: what does it measure, Sleep. 1982;5 Suppl 2:S67-72.
Carskadon, M. A., et al., Sleepiness in the normal adolescent. In: Sleep and it disorders in children, New York, Raven; 1987.
Carskadon, M. A., et al., Guidelines for the multiple sleep latency test (MSLT): a standard measure of sleepiness, Sleep. Dec. 1986;9(4):519-24.
Chervin, R. D., et al., Associations between symptoms of inattention, hyperactivity, restless legs, and periodic leg movements, Sleep. Mar. 15, 2002;25(2):213-8.
Corkum, P., et al., Sleep problems in children with attention-deficit/hyperactivity disorder: impact of subtype, comorbidity, and stimulant medication, J Am Acad Child Adolesc Psychiatry. Oct. 1999;38(10):1285-93.
Corkum, P., et al., Sleep disturbances in children with attention-deficit/hyperactivity disorder, J Am Acad Child Adolesc Psychiatry. Jun. 1998;37(6):637-46.
Cortese, S., et al., Restless legs syndrome and attention-deficit/hyperactivity disorder: a review of the literature, Sleep. Aug. 1, 2005;28(8):1007-13.
Golan, N., et al., Sleep disorders and daytime sleepiness in children with attention-deficit/hyperactive disorder, Sleep. Mar. 15, 2004;27(2):261-6.
Greenhill, L. L., et al., Sleep architecture and REM sleep measures in prepubertal children with attention deficit disorder with hyperactivity, Sleep. 1983;6(2):91-101.
Hadler, A. J., et al., Mazindol, a New Non-Amphetamine Anorexigenic Agent, J Clin Pharmacol New Drugs. Nov.-Dec. 1972;12(11):453-8.
Kaplan, B. J., et al., Sleep disturbance in preschool-aged hyperactive and nonhyperactive children, Pediatrics. Dec. 1987;80(6):839-44.

(Continued)

*Primary Examiner* — Johann Richter
*Assistant Examiner* — Jessica Kassa
(74) *Attorney, Agent, or Firm* — Pepper Hamilton LLP

(57) ABSTRACT

The present invention relates to the field of human health, and more particularly to the treatment of attention deficit/hyperactivity disorder (ADHD) with mazindol. The latter can be administered as monotherapy or in combination with one or more compounds, including psychostimulants, for the indication of ADHD and associated or co-morbid symptoms.

15 Claims, No Drawings

OTHER PUBLICATIONS

Konofal, E., et al., High levels of nocturnal activity in children with attention-deficit hyperactivity disorder: a video analysis, Psychiatry Clin Neurosci. Apr. 2001;55(2):97-103.

Konofal, E., et al., Iron deficiency in children with attention-deficit/hyperactivity disorder, Arch Pediatr Adolesc Med. Dec. 2004;158(12):1113-5.

Konofal, E., et al., Effectiveness of iron supplementation in a young child with attention-deficit/hyperactivity disorder, Pediatrics. Nov. 2005;116(5):e732-4.

Konofal, E., et al., Restless legs syndrome and attention-deficit/hyperactivity disorder, Ann Neurol. Aug. 2005;58(2):341-2; author reply 342.

Lecendreux, M., et al., Sleep and alertness in children with ADHD, J Child Psychol Psychiatry. Sep. 2000;41(6):803-12.

Mick, E., et al., Sleep disturbances associated with attention deficit hyperactivity disorder: the impact of psychiatric comorbidity and pharmacotherapy, J Child Adolesc Psychopharmacol. 2000 Fall;10(3):223-31.

Palm, L, et al., Sleep and wakefulness in preadolescent children with deficits in attention, motor control and perception, Acta Paediatr. Aug. 1992;81(8):618-24.

Picchietti, D. L., et al., Restless legs syndrome and periodic limb movement disorder in children and adolescents: comorbidity with attention-deficit/hyperactivity disorder, Child Adolesc. Psychiatry Clin N. Am, 1996;5:729-40.

Platon, M. J. R., et al., Hypnopolygraphic alterations in attention deficit disorder (ADD) children, Intern J Neurosci, 1990;53:87-101.

Popper, C. W., Pharmacologic alternatives to psychostimulants for the treatment of attention-deficit/hyperactivity disorder, Child Adolesc Psychiatr Clin N Am. Jul. 2000;9(3):605-46, viii.

Rugino, T. A., et al.,Effects of modafinil in children with attention-deficit/hyperactivity disorder: an open-label study, J Am Acad Child Adolesc Psychiatry. Feb. 2001;40(2):230-5.

Shindler, J., et al., Amphetamine, mazindol, and fencamfamin in narcolepsy, Br Med J (Clin Res Ed). Apr. 20, 1985;290(6476):1167-70.

Trommer, B. L., et al., Sleep disturbance in children with attention deficit disorder, Ann Neurology, 1988;24:322.

Walters, A. S., et al., Dopaminergic therapy in children with restless legs/periodic limb movements in sleep and ADHD. Dopaminergic Therapy Study Group, Pediatr Neurol. Mar. 2000;22(3):182-6.

Weinberg, W. A., et al., Primary disorder of vigilance: a novel explanation of inattentiveness, daydreaming, boredom, restlessness, and sleepiness, J Pediatr. May 1990;116(5):720-5.

Weinberg, W. A., et al., Vigilance and its disorders, Neurol Clin. Feb. 1993;11(1):59-78.

Weiss, M., et al., Adults with attention-deficit/hyperactivity disorder: current concepts, J Psychiatr Pract. Mar. 2002;8(2):99-111.

Walther, B. W., Treating restless legs syndrome: current pathophysiological concepts and clinical trials, Expert Opin Investig Drugs. Apr. 2002;11(4):501-14.

Vazquez-Alvarez, A., et al., Mazindol Effects on Lead—Induced Locomotor Hyperactivity in Mice, Biosciences Information Services, Philadelphia, PA 2002, Database accession No. PREV200300327254.

Zhou, J., Norepinephrine transporter inhibitors and their therapeutic potential, Drugs Future. Dec. 2004;29(12):1235-1244.

Lozoff, B., Behavioral Alterations in Iron Deficiency, Adv Pediatr, 1989; 6:331-59.

Zanin, M. et al., Sex Difference in Sensitization to the Locomotor Effects of Mazindol in Rats, Brain Research Bulletin, 1994;34(4):385-7.

Copeland, B. J., et al., Enhanced dopamine Uptake in the Striatum Following Repeated Restraint Stress, Synapse, 2005;57:167-174.

Picchietti, D. L., et al., Periodic Limb Movement Disorder and Restless Legs Syndrome in Children with Attention-deficit Hyperactivity Disorder, J Child Neurol., 1998;13:588-594.

Picchietti, D. L., et al., Further Studies on Periodic Limb Movement Disorder and Restless Legs Syndrome in Children with Attention-deficit Hyperactivity Disorder, Movement Disorders, 1999;14(6):1000-1007.

Gregory, A. M., et al., Sleep Problems in Childhood: A Longitudinal Study of Developmental Change and Association With Behavioral Problems, J. Am. Acad., Child Adoles. Psychiatry, Aug. 2002;41(8):964-971.

Gaultney, J. F., et al., Parent-Reported Periodic Limb Movement, Sleep Disordered Breathing, Bedtime Resistance Behaviors, and ADHD, Behavioral Sleep Medicine, 2005;3(1):32-43.

Chervin, R. D., et al., Symptoms of Sleep Disorders, Inattention, and Hyperactivity in Children, American Sleep Disorders Association and Sleep Research Society, 1997;20(12):1185-1192.

Spencer, T., et al., Nonstimulant treatment of adult attention-deficit/hyperactivity disorder, Psychiatr Clin N Am, 2004;27:373-383.

Enzi, G., et al., Short-Term and Long-Term Clinical Evaluation of a Non-Amphetaminic Anorexiant (Mazindol) in the Treatment of Obesity, J. Int. Med. Res., 1976;4:305-318.

* cited by examiner

MAZINDOL COMBINATION IN THE TREATMENT OF ATTENTION DEFICIT/HYPERACTIVITY

The present invention relates to the field of human health, and more particularly the treatment of attention-deficit/hyperactivity disorder (ADHD) with mazindol. The latter can be administered as monotherapy or in combination with one or more compounds, including psychostimulants, for the indication of ADHD and associated or co-morbid symptoms.

ADHD is a behavioural disorder that constitutes one of the most frequently encountered patterns in child and adolescent psychopathology. Its prevalence is estimated at 2% to 5% in the general population of children of school age.

On a clinical level, this disorder combines inattention, impulsivity and motor hyperactivity unsuited to the child's environment. Badly organised and thoughtless, these children sometimes end up not following in class. Excessive motor agitation, incompatible with social relations and sometimes even leading to being prematurely taken out of school, is probably the symptom that will lead the parents to consult a specialist.

The stimulating substances used, and commonly accepted in the pharmacological treatment of ADHD, in particular in children, belong to several pharmacological classes: psychostimulants (amphetamine, methylphenidate, bupropion), eugregorics (Modafinil, Adrafinil), and inhibitors of monoamine oxydase B (selegiline).

The most used and best known are:
methylphenidate (MPH) is the reference treatment of ADHD in children, adolescents and adults. It is above all a psychostimulant known for its stimulating properties. Apart from its dopaminergic stimulating action, on the release of noradrenaline and dopamine, by inhibition and recapture, MPH has no effect on the postsynaptic noradrenergic alpha-1 receptors (modification of sensitivity).
amphetamine (D,L-amphetamine) has an action on the extra-vesicular release of noradrenaline and dopamine and therefore inhibits any form of storage. Because of potential misuse, and undesirable peripheral effects (tachycardia, HTA, agitation, insomnia) its medication remains very limited and non-authorised in the majority of countries in Europe.
Modafinil, the authorisation of which for the treatment of ADHD in children has just been granted recently in the United States (2005), is a stimulating (eugregoric) medication whose action mechanism, which is complex, is imperfectly known. Unlike MPH and amphetamines, Modafinil does not cause dependency or habituation. Its prescription is at the present time limited in France to the treatment of narcolepsy and idiopathic hypersomnia.
Atomoxetine, a selective inhibitor of the recapture of noradrenaline, and a dopaminogenic stimulant (by inhibiting recapture at the pre-frontal cortex), has demonstrated efficacy and good tolerance in ADHD in children and adults (Spencer et al, 1998; Popper 2000; Biederman et al, 2002). It has recently been authorised for marketing in the United States (FDA, November, 2002).
others: bupropion, caffeine, selegiline, etc.

Bupropion, a catecholamine uptake inhibitor, and an antidepressant, is also a potential competitor in the treatment of ADHD.

Selegiline, a mono-oxidase uptake inhibitor, also has pharmacological properties close to those of amphetamines. Its stimulating action in the treatment of ADHD is known and its advantage in this use is possible.

Thus the improvement of motive hyperactivity by dopaminergic psychostimulants is often very significant, but nevertheless insufficient.

This is because the stimulating substances used or which could be used in the treatment of ADHD, in particular psychostimulants such as methylphenidate or amphetamines, often have a short plasmatic half-life, which involves the appearance of "on-off" effects, that is to say a coming-off effect that is accompanied by a "symptom rebound" effect after a few hours and is responsible for a worsening of the symptoms in the last part of the night, and detrimental to the quality of falling asleep.

In addition, some of these substances are metabolised in the organism and therefore present a toxic risk for the patient.

In addition, some of the medications administered in the treatment of ADHD are not suited to particular administration to children, especially because of excessive size of the tablets or the administration of the medications several times a day.

In addition, certain particular symptoms such as insomnia, difficulties in falling asleep, waking during the night, possibly due to excessive nocturnal motive agitation, as well as additional disorders such as inattention, impatience and impulsivity, seem to resist any form of treatment [Chervin et al, Associations between symptoms of inattention, hyperactivity, restless legs, and periodic leg movements. Sleep 2002 15; 25(2):213-8; Gruber et al, instability of sleep patterns in children with attention-deficit/hyperactivity disorder. J Am Acad Child Adolesc Psychiatry. 2000; 39(4):495-501].

There therefore exists a real need to develop new treatments for ADHD that make it possible to obtain results superior to those obtained with current treatments based on psychostimulants and in particular to be able to treat the symptoms that resist current treatments, without any coming-off effect or rebound of the symptoms and presenting limited toxic risk. Treatments intended more particularly for children are advantageously sought. This is the aim of the present invention.

Entirely fortuitously, studies have now shown that mazindol could be used for the preventive and curative treatment of ADHD with significant results, without the previously mentioned drawbacks of the other substances, in particular certain psychostimulants.

Mazindol has the following chemical formula:

5-(4-chlorophenyl)-2,5-dihydro-3H-imadazo[2,1-a] isoindol-5-ol

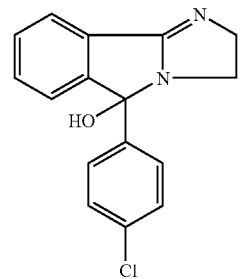

Mazindol is considered, in current medication classifications, as a phsycoanaleptic and anorexigenic medication, but also as giving rise to wakefulness, currently not authorised in France, or only authorised by TAU (temporary authorisation for use) in obesity and narcolepsy. It is an advantageous chemical compound for dealing with malfunctioning of wakefulness mechanisms.

The essential pharmacological action of mazindol, in all species studied, in healthy animals and in humans, is hypothalamic, on the appetite-regulating dopaminogenic centres (Hadler, 1972). Its principal metabolism is urinary (¾ urine, ¼ faeces).

Mazindol is a non-amphetamine compound because of its tricyclic chemical structure. It offers a pharmacological profile very close to that of amphetamines without reproducing the secondary effects thereof. Thus, unlike amphetamine molecules, mazindol increases motor activity only in relation to extension of the duration of wakefulness and does not cause cardiovascular modifications or stereotypes (Hadler, 1972).

In addition, in animal toxicology studies, the toxic potential of mazindol has proved to be very low. This is because mazindol presents a limited toxic risk since the metabolites of mazindol are excreted in the urine. In particular:

no carcinogenic effect;
no mutagenic effect;
no toxicology effect in reproduction were observed.

In addition, mazindol has a long plasmatic half-life time, greater than one day, which avoids the appearance of coming-off effects, and therefore an effect of "symptom rebound" at the end of the day.

In fact, after single or repeated oral administration, mazindol is absorbed with a tmax of 2-4 hours. Taking food concomitantly is liable to delay absorption (by approximately 1 hour), but does not modify the total quantity absorbed. The plasmatic half-life time is reached after 33-55 hours.

The pharmacokinetics is linear (independent of the dose) for doses of between 1 mg/day and 4 mg/day, and 75% of the dose is still "plasmatically" effective 24 hours after taking.

In addition, mazindol (Teronac®) tablets are small and therefore do not pose any problem in administration. For pharmacokinetic reasons, already cited, mazindol is administered only once a day, which limits constraints for the patient, and in particular in the special case of children for the school, which is often requested to perform the midday administration.

Mazindol has for more than 30 years been the subject of many double blind control studies against a placebo on the treatment of obesity in adults. Studies in the treatment of narcolepsy and hypersomnia are limited. On the other hand, safety in use in the short, medium and long term in the treatment of excessive daytime somnolence associated with narcolepsy and idiopathic hypersomnia is relatively well documented for the time (Shindler et al, 1985).

Mazindol has in these two disorders (narcolepsy and hypersomnia) become a TAU (Temporary Authorisation for Use) treatment by third intention that significantly improves the quality of life of the patient having difficulty in keeping awake.

The object of the present invention is therefore the use of mazindol for the preparation of a medication intended for the preventive and/or curative treatment of attention-deficit/hyperactivity disorder (ADHD) or at least one of its symptoms, in a patient in need of such treatment.

In the context of the present invention, the diagnosis of attention-deficit/hyperactivity disorder (ADHD) is based on the clinical characteristics defined by the international classification, DSM/IV (Diagnostic and Statistical Manual of Mental Disorders, 4th ed, 1994).

The criteria of DSM-IV includes three dimensions (inattention, impulsivity and hyperactivity), normal intellectual efficiency (IQ>80, with an age between 5 and 12 years) and having isolated iron deficiency, but not anaemic, that is to say having a normal haemoglobin level. The expression "iron deficiency" means hypoferrinaemia without significant modification to the serum concentration of soluble transferrin receptors.

The patient according to the invention is chosen from among a newborn baby, a child, an adolescent and an adult. According to a preferential embodiment, it is a case of a child aged approximately 5 to 12 years, and/or for an adolescent. The patient according to the invention advantageously suffers iron deficiency, but is not anaemic. Ferritin deficiency can be measured in the serum, but also in all other biological fluids such as the cerebrospinal fluid.

A ferritin deficiency corresponds to a serum concentration of ferritin in the adult patient of less than approximately 50 µg/liter. This hypoferritinaemia may reach ferritin concentrations of less than approximately 40 µg/l, or even less than approximately 35 µg/l, less than 30 µg/l, less than 20 µg/l, less than 15 µg/l, or even less than approximately 10 µg/l. The techniques of determining serum ferritin are well known to persons skilled in the art. The immunoenzymatic method (IMX ferritin kit, Abbot Laboratories) can be cited.

The patient according to the invention also has a normal serum concentration of receptors soluble to transferrin. Transferrin is involved in the acquisition of iron by the cells of the organism; this acquisition is controlled by the number of transferrin receptors existing on the cell surface. The concentration of these receptors can be evaluated by techniques known to persons skilled in the art such as nephelemetry (Ruivard et al. 2000 Rev Méd Interne 21: 837-843). A normal range of concentration of receptors soluble to transferrin is 2.0-4.50 mg/l for men and 1.80-4.70 mg/l for women (see RsTF kit Ref 2148315 from Roche).

The compounds or compositions according to the invention can be administered in various ways and in different forms. Thus they can be administered systemically, orally, anally or parentally, in particular by inhalation or injection, such as for example by intravenous, intramuscular, subcutaneous, transdermal or intra-arterial method. Preferably it is orally.

For injections, the compounds are generally packaged in the form of liquid suspensions, which may be injected by means of syringes or perfusions for example. In this regard the compounds are generally dissolved in saline, physiological, isotonic, buffer, etc., solutions, compatible with pharmaceutical usage and known to persons skilled in the art. Thus the compositions may contain one or more agents or vehicles chosen from dispersants, solubilisers, stabilisers, preservatives, etc. Agents or vehicles that can be used in liquid and/or injectable formulations are in particular methylcellulose, hydroxymethylcellulose, carboxymethylcellulose, polysorbate 80, mannitol, gelatine, lactose, vegetable oils, acacia, etc.

The compounds can also be administered in the form of gels, oils, tablets, suppositories, powders, capsules, aerosols, etc, possibly by means of galenic forms or devices providing prolonged and/or delayed release. For this type of formulation, use is advantageously made of an agent such as cellulose, carbonates or starches.

"ADHD symptom" designates in particular attention disorders such as inattention, impulsivity, impatience, oppositional disorders, but also daytime or night-time motor hyperactivity, restless legs syndrome, and insomnia.

Insomnia designates:
a. onset insomnia that is characterised by difficulties in falling asleep;
b. maintenance insomnia that is characterised by night-time motor hyperactivity and waking up during the night, and c. psychopathological insomnia, generally chronic and generally linked to anxiety, stress and depressive episodes.

According to another aspect of the present invention, mazindol is used in combination with iron as a combination product for simultaneous, separate or sequential use.

According to a preferred method of use, the iron is used as a supplement with the patient before the administration of mazindol.

Within the meaning of the present invention, "iron" means iron in the form of an iron atom, iron salt or organic iron, or any formulation containing iron that is pharmaceutically acceptable. By way of a non-exhaustive list, the pharmaceutically acceptable iron salt is selected from ferrous salts and ferric salts, preferably from ferric ammonium citrate, ferric pyrophosphate, ferrocholinate, ferrous abscorbate, ferrous aspartate, ferrous chloride, ferrous sulphate, ferrous tartatrate, ferrous fumatrate, ferrous gluconate, ferrous gluceptate, ferrous sulphate glycine, ferrous lactate, ferrous oxalate and ferrous succinate.

According to a preferred embodiment of the invention, the iron salt is ferrous sulphate, and preferably gastro-protected ferrous sulphate.

Alternatively, the pharmaceutical acceptable iron is in the form of dextran iron, sucrose iron, poly-maltose iron, or sorbitol iron. When the iron is in the form of pharmaceutically acceptable organic iron, it is preferably iron biglycinate, iron glycinate or iron protein succinylate.

According to a preferred embodiment, the use of mazindol possibly in association with the iron according to the invention is implemented in combination with at least one compound selected from psychostimulants, as a combination product for simultaneous, separate or sequential use.

Psychostimulant compounds designate dopamine and/or noradrenaline uptake inhibitors and agonists of catecholamines. Among these, the following can be cited non-exhaustively:

1) psychostimulant compounds: methylphenidate (speciality Ritalin, Concerta, Equasym), modafinil (Sparlon, Modiodal, Provigil), atomoxetine (Strattera), and amphetamines such as d-amphetamine, dexadrine and dexamphetamine.

2) L-Dopa: Modopar, Sinemat 3) selective dopamine agonists: pramipexole (Sifrol, Mirapex), ropinirole (Requip, Adartrel), lisuride, pergolide, cabergoline, etc.

The role of iron with regard to the central nervous system is often reported in fundamental neurophysiopathology as clinical. Functional intellectual asthenia, chronic fatigue syndrome, or conversely psychomotive instability and irritability may be the consequence of iron deficiency (Lozoff, 1989 Adv Pediatr 1989; 6:331-59). The role of iron in the physiopathology of neurological ailments, and in particular in idiopathic Parkinson's disease, has been known for more than thirty years. The evidence of an increase in iron in particular in certain cerebral structures (e.g. dentate nucleus) in rare neurodegenerative pathologies (e.g. Friedreich's ataxia) is also known. More recently, the role of transferrin receptors in certain neuropathological processes has just been documented (Marder F et al, 1998 Neurology 50, 4:1138-40). An increase in number of transferrin receptors in cells of the endothelium of the cerebral capillaries could be responsible for the accumulation of basal ganglia (globus pallidus, substantia nigra, red nucleus and dentate nucleus). A malfunctioning of the transferrin receptors by hyperplasia (increase in the number of receptors) at a central level would explain the accumulation of iron in certain structures involved in phenomena of neurodegenerescence. On the other hand, a reduction in these receptors would contribute to protecting the central nuclei from the phenomenon. On the assumption of a decrease in plasma ferritin in ADHD physiopathology, a physiological increase in the transferrin receptors should occur, as occurs normally in cases of anaemia, in order not to put the cerebral structures in iron deficiency. On the other hand, an absence of response (an absence of increase in the number of transferrin receptors) would lead to a cerebral iron reduction and would be compatible with dopamine malfunctioning by reducing its synthesis and/or stimulating the dopaminergic receptors. The present invention therefore also concerns the use of mazindol, optionally in association with iron or one of its pharmaceutically acceptable salts, and/or a psychostimulant for the preventive treatment of a newborn, infant, adolescent or young adult patient caused to develop a neurodegenerative pathology at an adult age, characterised in that the said newborn, infant, adolescent or young adult patient has at least the following symptoms:

ferritin deficiency, so that the serum concentration of ferritin is less than 50 µg/l;

a normal serum concentration of receptors soluble to transferrin;

attention-deficit/hyperactivity disorder, or at least one of its symptoms.

Preferably the said patient is a child with an IQ>80, aged between approximately 5 and 12 years and non-anaemic.

Preferably the said neurodegenerative pathology is Parkinson's disease, cerebellar ataxia, Friedreich's ataxia, Alzheimer's disease, Huntingdon's chorea or amyotrophic lateral sclerosis. More particularly, it is Parkinson's disease.

In particular, when mazindol is used in association with ferrous sulphate, the quantity of ferrous sulphate administered to the patient on a daily basis is between 0.1 mg and 10 mg, preferably between 100 mg and 2 g per day, preferably approximately 500 mg, in one or more doses.

More particularly, according to the present invention, the patients undergo iron supplementation, in particular ferrous sulphate, for 12 weeks and the treatment with mazindol for 12 weeks.

The dosage corresponds to a daily dose of mazindol preferably between 1 and 2 mg (recommended doses in the treatment of narcolepsy in adults).

The criteria for evaluating the efficacy of the treatment of attention-deficit/hyperactivity disorder by mazindol optionally in association with iron and/or a psychostimulant in the treatment of attention-deficit/hyperactivity disorder according to the present invention are the reduction (>30%) in the rating scale severity score for attention-deficit/hyperactivity symptoms AHD-RS (after 12 weeks of treatment, and an improvement in severity scores for Conner's Parent questionnaire (CPRS), Conner's Teacher questionnaire (CTRS) and CGI (clinical global impressions). Subjective somnolence is assessed using the CASS scale (child and adolescent somnolence scale). The quality of falling asleep is assessed by means of the restless legs syndrome severity scale.

Finally, the present invention also concerns a pharmaceutical composition comprising pharmaceutically acceptable excipients and mazindol for the preventive and/or curative treatment of ADHD or one of its symptoms.

According to the present invention, the composition may also comprise iron or one of its pharmaceutically acceptable salts and/or a psychostimulant.

REFERENCES

Biederman J, Swanson J M, Wigal S B, Kratochvil C J, Boeflner S W, Earl C Q, Jiang J, Greenhill L. Efficacy and safety of modafinil film-coated tablets in children and adolescents with attention-deficit/hyperactivity disorder: results of a randomised, double-blind, placebo-controlled, flexible-dose study, Pediatrics 116: e777 2005

Biederman J. Heiligenstein J H, Fanes D E, Galil N, Dittmann R, Emslie G J, Kratochvil C J, Laws H F, Schuh K J, Efficacy of atomoxetine versus placebo in school-age girls with attention-deficit/hyperactivity disorder. Pediatrics 110 (6): 75; 2002

Busby K, Firestone P, Pivik R T—Sleep pattern in hyperkinetic and normal children. Sleep, 4, 366-83; 1981

Carskadon M A, Dement W C—Sleepiness in the normal adolescent. In: Sleep and its disorders in children. New York, Raven; 1987

Carskadon M A, Dement W C—The multiple sleep latency test: what does R measure? Sleep, 5, S67-72; 1982

Carskadon M A, Dement W C, Mitler M M, Roth T, Westbrook P R, Keenan S—Guidelines for the Multiple Sleep Latency Test (MSLT): a standard measure of sleepiness. Sleep 9:519-24; 1986

Chervin R D, Archbold K H, Dillon J E, Pituch K J, Panahi P, Dahl R E, Guilleminault C, Associations between symptoms of inattention, hyperactivity, restless legs, and periodic leg movements. Sleep 15; 25(2):213-8; 2002

Corkum P, Moldofsky H, Hogg-Johnson, Humphries T, Tannock R—Sleep problems in children with attention-deficit/hyperactivity disorder: impact of Subtype, comorbidity, and stimulant medication. J Am Acad Child Adolesc Psychiatry 38, 1285-93; 1999

Corkum P, Tannock R, Moldofsky H—Sleep disturbances in children with attention-deficit/hyperactivity disorder. J Am Acad Child Adolesc Psychiatry 37, 6, 637-46; 1998

Cortese S, Konofal E, Lecendreux M, Arnulf I, Mouren M C, Darra F, Dalla Bernardine B. Restless legs syndrome and attention-deficit/hyperactivity disorder: a review of the literature. Sleep. 2005; 28(8):1007-13.

Golan N, Shahar E, Ravid S, Pillar G. Sleep disorders and daytime sleepiness in children with attention-deficit/hyperactivity disorder. Sleep. 15; 27:261-6; 2004

Greenhill L L, Puig-Antich J, Goetz R, Hanlon C—Sleep architecture and REM sleep measure in prebutertal children with attention deficit disorder with hyperactivity. Sleep 6, 91-101; 1983

Hadier A J, mazindol, a new non-amphetamine anorexigenic agent. J Clin Pharmacol New Drugs. 12:453-8. 1972

Kaplan B J, McNicol J, Conte R A, Moghadam H K. Sleep disturbance in preschool aged hyperactive and nonhyperactive children. Pediatrics 80: 839-44; 1987

Konofal E, Lecendreux M, Bouvard M and Mouren-Siméoni M-C. High levels of nocturnal activity in children with ADHD: a video analysis. Psychiatry Clin Neurosci 55, 2, 97-103; 2001

Konafal E, Lecendreux M, Mouren-Simeoni M-C. Sleep in children with attention-deficit/hyperactivity disorder: a restatement on sleep studies. Ann Med Psychol 160:105-17; 2002

Konofal E, Lecendreux M, Arnulf I, Mouren M C. Iron deficiency in children with attention-deficit/hyperactivity disorder. Arch Pediatr Adolesc Med. 2004; 158(12):1 113-5

Konofal E, Cortese S, Lecendreux M, Arnulf I, Mouren M C. Effectiveness of Iron supplementation in a young child with attention-deficit/hyperactivity disorder. Pediatrics 2005; 116(5).

Konofal E, Cortese S. Resless legs syndrome and attention-deficit/hyperactivity disorder.
Ann Neurol. 2005; 58(2):341-2

Lecendreux M, Konofal E, Bouvard M, Falissard B, Mouren-Simeoni M-C—Sleep and alertness in children with ADHD. J Child Psychol Psychiatry 41, 6, 803-12; 2000

Mick E, Biederman J, Jetton J, Faraone S V. Sleep disturbances associated with attention-deficit/hyperactivity disorder: the impact of psychiatric comorbidity and pharmacotherapy. J Child Adolesc Psychopharmacol Fall 10, 3:223-31; 2000

Palm L, Persson E, Bjerre L, Elmqvist D—Sleep and wakefulness in preadolescent children with deficits in attention, motor control and perception. Acta Paediatr 81, 618-24; 1992

Picchietti D L, Walters A s—Restless legs syndrome and periodic limb movement disorder in children and adolescents: comorbidity with attention-deficit/hyperactivity disorder. Child Adolesc. Psychiatry Clin N Am 5, 729-40; 1996

Platon M J R, Vela Bueno A, Espinar Sierra J, Kales S—Hypnopolygraphic alterations in attention deficit disorder (ADD) children. Intern J Neurosci 53, 87-101; 1990

Popper C W—Pharmacologic alternatives to psychostimulants for the treatment of attention-deficit/hyperactivity disorder. Child Adolesc Psychiatr Clin N Am 9, 3,605-46; 2000

Rugino T A, Copley T C. Effects of modafinil in children with attention-deficit/hyperactivity disorder: an open study. J Am Acad Child Adolesc Psychiatry 40(2):230-5; 2001

Schindler J, Schachter M, Brincat S, Parkes J D. Amphetamine, mazindol, and fencamfamin in narcolepsy. Br Med J. 20; 1167-70; 1985

Trommer B L, Hoeppner J B, Rosenberg R S, Armstrong K J, Rothstein J A. Sleep disturbance in children with attention deficit disorder. Ann Neurology 24: 322; 1988

Walters A S, Mandelbaum D E, Lewin D S, Kugler S, England S J, Miller M—Dopaminergic therapy in children with restless legs/periodic limb movements in sleep and ADHD. Dopaminergic Therapy Study Group. Pediatr Neurol 22, 3, 182-6; 2000

Weinberg A S, Brumback R A—Primary disorder of vigilance: a novel explanation of inattentiveness, daydreaming, boredom, restlessness, and sleepiness. J Pediatr 116, 720-5; 1992

Weinberg W A, Harper C R—Vigilance and its disorders. Neurol Clin 11, 59-78; 1993

Weis M, Murray C, Weiss G. Adults with attention-deficit/hyperactivity disorder: current concepts. J Psychiatr Pract. 28, 99-111; 2002

The invention claimed is:

1. A method of treating attention-deficit/hyperactivity disorder (ADHD) according to the DSM IV criteria, comprising the administration of an effective amount of mazindol in the absence of another active agent to a patient in need of such treatment.

2. The method according to claim 1, wherein said patient is chosen from a newborn baby, a child, an adolescent, and an adult.

3. The method according to claim 2, wherein said patient is a child having isolated iron deficiency, but not anaemic.

4. The method according to claim 1, wherein mazindol is formulated to allow its administration by oral, anal, parenteral, intra-muscular or intravenous method.

5. The method according to claim 1, wherein the dosage corresponds to a daily dose of mazindol of between 1 and 2 mg.

6. The method according to claim 1, wherein said patient suffers from ferritin deficiency, said serum ferritin concentration of said patient being less than 50 µg/liter, less than approximately 40 µg/l, less than approximately 35 µg/l, less than approximately 30 µg/l, less than approximately 20 µg/l, less than approximately 15 µg/l, less than approximately 10 µg/l or less than approximately 5 µg/l.

7. The method according to claim 6, wherein said patient also has a normal serum concentration of transferrin-soluble receptors.

8. The method according to claim 1 for the treatment of a newborn, adolescent or young adult patient having at least one of the following symptoms:
- a ferritin deficiency, so that the serum ferritin concentration is less than 50 µg/l,
- a normal serum concentration of transferrin-soluble receptors,
- attention-deficit/hyperactivity disorder according to the DSM IV criteria.

9. A method of treating attention-deficit/hyperactivity disorder (ADHD) according to the DSM IV criteria, comprising administering an effective amount of mazindol simultaneously, separately or sequentially with iron to a patient in need of such treatment, wherein mazindol and iron are the only active ingredients.

10. The method according to claim 9, wherein the patient is chosen from a newborn baby, a child, an adolescent, and an adult.

11. The method according to claim 10, wherein the patient is a child having isolated iron deficiency, but not anaemic.

12. The method according to claim 9, wherein mazindol is formulated to allow its administration by oral, anal, parenteral, intra-muscular or intravenous method.

13. The method according to claim 9, wherein the dosage corresponds to a daily dose of mazindol of between 1 and 2 mg.

14. The method according to claim 9, wherein the patient suffers from ferritin deficiency, wherein the serum ferritin concentration of the patient is less than 50 µg/liter, less than approximately 40 µg/l, less than approximately 35 µg/l, less than approximately 30 µg/l, less than approximately 20 µg/l, less than approximately 15 µg/l, less than approximately 10 µg/l, or less than approximately 5 µg/l.

15. The method according to claim 14, wherein the patient also has a normal serum concentration of transferrin-soluble receptors.

* * * * *